US012727574B2

(12) United States Patent
Whitaker

(10) Patent No.: US 12,727,574 B2
(45) **Date of Patent: *Sep. 8, 2026**

(54) STRAWBERRY VARIETY 'FL 20.34-183'

(71) Applicant: University of Florida Research Foundation, Inc., Gainesville, FL (US)

(72) Inventor: Vance M. Whitaker, Brandon, FL (US)

(73) Assignees: UNIVERSITY OF FLORIDA RESEARCH FOUNDATION, INC., Gainesville, FL (US); FLORIDA FOUNDATION SEED PRODUCERS, INC., Marianna, FL (US)

( * ) Notice: Subject to any disclaimer, the term of this patent is extended or adjusted under 35 U.S.C. 154(b) by 183 days.

This patent is subject to a terminal disclaimer.

(21) Appl. No.: 18/424,392

(22) Filed: Jan. 26, 2024

(65) Prior Publication Data

US 2025/0241266 A1 Jul. 31, 2025

(51) Int. Cl.
*A01H 5/08* (2018.01)
*A01H 1/00* (2006.01)
*A01H 6/74* (2018.01)

(52) U.S. Cl.
CPC ............. *A01H 6/7409* (2018.05); *A01H 1/00* (2013.01); *A01H 5/08* (2013.01)

(58) Field of Classification Search
None
See application file for complete search history.

(56) References Cited

U.S. PATENT DOCUMENTS

PP25,574 P3 5/2015 Whitaker et al.
PP30,564 P3 6/2019 Whitaker
PP31,912 P2 * 6/2020 Bourne .................... A01H 6/88 Plt./205

OTHER PUBLICATIONS

U.S. Appl. No. 18/407,889, filed Jan. 9, 2024, Whitaker.
U.S. Appl. No. 18/407,954 filed Jan. 9, 2024, Whitaker.
U.S. Appl. No. 18/424,399, filed Jan. 26, 2024, Whitaker.
Bassil, et al., "Development and preliminary evaluation of a 90 K Axiom® SNP array for the allo-octoploid cultivated strawberry *Fragaria x ananassa*." BMC Genomics, 16, 155, (2015).
Edger, et al., "Origin and evolution of the octoploid strawberry genome." Nature Genetics, 51, 541-547 (2019).
Hardigan, et al., "Genome Synteny Has Been Conserved Among the Octoploid Progenitors of Cultivated Strawberry Over Millions of Years of Evolution." Frontiers in Plant Science, 10, 1789 (2020).
Moose and Mumm, "Molecular Plant Breeding as the Foundation for 21st Century Crop Improvement." Plant Physiology, 147: 969-977, (2008).
Porter, et al., "Strawberry breeding for improved flavor." Crop Science, 63, 1949-1963 (2023).
Sauer, et al., "Oligonucleotide-Mediated Genome Editing Provides Precision and Function to Engineered Nucleases and Antibiotics in Plants." Plant Physiol, 170(4):1917-1928, (2016).
Wang, et al., "CRISPR/Cas9-Based Mutagenesis of Starch Biosynthetic Genes in Sweet Potato (*Ipomoea batatas*) for the Improvement of Starch Quality." Int. J. Mol. Sci. 20(19):4702, (2019).
Zakaria, et al., "Improved regeneration and transformation protocols for three strawberry cultivars." GM Crops Food. Biotechnology in Agriculture and the Food Chain 5(1), 27-35, (2014).

* cited by examiner

*Primary Examiner* — Phuong T Bui
(74) *Attorney, Agent, or Firm* — Dentons US LLP

(57) ABSTRACT

The invention provides plants of the strawberry variety designated 'FL 20.34-183'. The invention thus relates to the plants, cells, plant parts, and tissue cultures of variety 'FL 20.34-183', and to methods for producing a strawberry plant produced by crossing a strawberry plant of strawberry variety 'FL 20.34-183' with another strawberry plant, such as a plant of another variety. The invention further relates to strawberry seeds and plants produced by crossing plants of variety 'FL 20.34-183' with plants of another variety.

18 Claims, 2 Drawing Sheets

Performance of three strawberry genotypes during the 2022-2023 season in Balm, Florida

| Cultivar | Marketable yield (g/plant) | | | | | | | | | | | | | |
|---|---|---|---|---|---|---|---|---|---|---|---|---|---|---|
| | November | | December | | January | | February | | March | | Total | | Wt/fruit(g)[z] | |
| 'Florida Brilliance' | 15.9 | b[y] | 78.2 | ab | 185.5 | a | 592.5 | a | 348.7 | a | 1220.8 | a | 24.9 | b |
| 'Florida127' | 22.6 | ab | 66.7 | b | 162.0 | a | 534.1 | a | 203.8 | b | 989.2 | b | 28.2 | a |
| 'FL 20.34-183' | 30.1 | a | 89.0 | a | 188.4 | a | 514.5 | a | 345.3 | a | 1167.3 | a | 26.6 | ab |

[z] Mean fruit weight was determined by dividing total marketable fruit yield per plot by total marketable fruit number per plot.

[y] Mean separation within columns is by Tukey's HSD test, $P \leq 0.05$.

FIG. 2

STRAWBERRY VARIETY 'FL 20.34-183'

BACKGROUND OF THE INVENTION

Field of the Invention

The present invention relates to the field of plant breeding and, more specifically, to a new and distinctive strawberry variety, designated 'FL 20.34-183', and derivatives and tissue cultures thereof. All publications cited in this application are herein incorporated by reference.

Background of the Invention

Strawberry (*Fragaria×ananassa* Duchesne) is cultivated and enjoyed globally for its health properties and flavor. The strawberry is one of the most widely distributed berry crops in the world. Production of strawberries was 8.9 million metric tons in 2020 (FAOSTAT, 2020) with 43% in Asia, 26.9% in the Americas, and 24% in Europe. In the United States, annualized production in California and Florida in open fields provides the bulk of supermarket strawberries, whereas high tunnel and greenhouse production systems predominate in Europe and some other regions. Commercial production is concentrated in relatively warm climatic areas that can provide fresh strawberries for much of the year.

Strawberries are clonally multiplied via stolons or "runners". Thus, the vast majority of cultivars are clonal. While single varieties planted in monocultures readily self-pollinate during fruit production, selfing can result in severe inbreeding depression in the offspring (Shaw, *Theoretical and Applied Genetics,* 90 (2), 237-241 (1995)). Thus, a pedigree breeding scheme is typical for strawberry, with full-sib crosses and even half-sib crosses often avoided. Visual evaluations are used for screening seedlings before clonal testing of selections provides the opportunity to screen for various traits and in multiple environments. As an allo-octoploid (2n=8×=56) species, genetic studies have historically been complicated by a lack of molecular marker and other genomic resources. However, recent studies have significantly advances strawberry genomics and breeding research. See, e.g. Bassil et al., *Genomics,* 16 (1), 1310 (2015); Edger et al., *Nature Genetics,* 51 (3), 541-547 (2019); and Hardigan et al., *Frontiers in Plant Science,* 10, 1789 (2019).

Improvements in agronomic performance and fruit quality attributes highlight the successes of strawberry breeding in recent decades. Nevertheless, sweetness and flavor continue to fall below the ideal for the average consumer. Flavor is therefore an important trait of focus during variety development, and is one of many critical traits necessary for the success of a strawberry variety. Strawberry breeders must also take into consideration, e.g. fruit yield, fruit size, fruit shape, time of flowering and fruiting, fruit firmness, and disease resistance. Thus, a continuing need exists in the art to develop new strawberry varieties with desirable combinations of agronomic characteristics including improved flavor intensity and complexity.

SUMMARY OF THE INVENTION

In one aspect, the present invention provides a strawberry plant of variety 'FL 20.34-183'. Also provided are strawberry plants having all the physiological and morphological characteristics of such a plant. Parts of the strawberry plant of the present invention are also provided, including e.g. a flower, pollen, a leaf, an ovule, an embryo, a cutting, a stem, a seed, a fruit, and a cell of the plant. In other embodiments, a tissue culture of regenerable cells of a strawberry plant of variety 'FL 20.34-183' are also provided. The tissue culture will preferably be capable of regenerating strawberry plants capable of expressing all of the physiological and morphological characteristics of the starting plant, and of regenerating plants having substantially the same genotype as the starting plant. Examples of some of the physiological and morphological characteristics of the variety 'FL 20.34-183' include those traits set forth herein. The regenerable cells in such tissue cultures may be derived, for example, from embryos, meristems, pollen, leaves, anthers, roots, root tips, pistils, and flowers. In further embodiments, a strawberry plant regenerated from the tissue culture, wherein the regenerated plant comprises all of the physiological and morphological characteristics of strawberry variety 'FL 20.34-183' is provided.

In another aspect, a method for producing a seed of a strawberry plant derived from strawberry variety 'FL 20.34-183' is provided, wherein the method comprises the steps of: crossing a strawberry plant of variety 'FL 20.34-183' with itself or a second strawberry plant; and allowing seed of a strawberry variety 'FL 20.34-183'-derived strawberry plant to form. In some embodiments, the method further comprises crossing a plant grown from said 'FL 20.34-183'-derived strawberry seed with itself or a second strawberry plant to yield additional 'FL 20.34-183'-derived strawberry seed; growing said additional 'FL 20.34-183'-derived strawberry seed to yield additional 'FL 20.34-183'-derived strawberry plants; and repeating said crossing and growing steps to generate further 'FL 20.34-183'-derived strawberry plants.

In another aspect of the invention, a method of vegetatively propagating a strawberry plant of variety 'FL 20.34-183' is provided, wherein the method comprises collecting tissue capable of being propagated from a plant of variety 'FL 20.34-183'; and propagating a strawberry plant from the tissue.

In yet another aspect of the invention, methods of introducing a trait into a strawberry plant are provided. In one embodiment, the method comprises utilizing as a recurrent parent a plant of strawberry variety 'FL 20.34-183' by crossing the plant with a donor strawberry plant that comprises the trait to produce F1 progeny; selecting an F1 progeny that comprises the trait; backcrossing the selected F1 progeny with a plant of the same strawberry variety used as a recurrent parent in step to produce backcross progeny; selecting a backcross progeny that comprises the trait; and repeating the backcrossing and selecting steps at least one more time to produce a selected second or higher backcross. In specific embodiments, the backcross progeny comprises the trait and otherwise comprises all of the physiological and morphological characteristics of a strawberry plant of variety 'FL 20.34-183'.

In another aspect of the invention, a plant of strawberry variety 'FL 20.34-183' comprising an added heritable trait is provided. In one embodiment, a plant of strawberry variety 'FL 20.34-183' is defined as comprising a single locus conversion. In specific embodiments, an added genetic locus confers one or more traits such as, for example, herbicide tolerance, insect resistance, pest resistance, disease resistance, modified fatty acid metabolism, environmental stress tolerance, modified carbohydrate metabolism, improved fruit size, improved fruit shape, improved firmness, increased yield, enhanced fruit flavor, and increased shelf-life. In further embodiments, the trait may be conferred by a naturally occurring gene introduced into the genome of a line by backcrossing, a natural or induced mutation, or a transgene introduced through genetic transformation techniques into the plant or a progenitor of any previous generation thereof. When introduced through transformation, a genetic locus may comprise one or more genes integrated at a single chromosomal location.

In yet another aspect of the invention, a method of producing a strawberry fruit is provided comprising obtaining a plant of strawberry variety 'FL 20.34-183', wherein the plant has been cultivated to maturity, and collecting at least one strawberry fruit from the plant.

BRIEF DESCRIPTION OF THE DRAWINGS

FIG. 2 shows a comparison of marketable yield (g/plant) between strawberry variety 'Florida Brilliance', 'Florida127', and 'FL 20.34-183' during the 2022-2023 season in Balm, Florida.

DETAILED DESCRIPTION OF THE INVENTION

Definitions

Figure 1:
FIG. 1 shows fruit from 5-month-old plants of new strawberry variety 'FL 20.34-183' at varying stages of ripeness. These photographs show the colors as true as can be reasonably captured by conventional photographic procedures. Colors in the photographs may differ slightly from the color values cited in the detailed botanical description, which accurately describe the colors of the new strawberry variety. The photograph was captured in March of 2023 in West Central Florida.

Allele: Any of one or more alternative forms of a gene locus, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny back to one of the parents, for example, a first generation hybrid ($F_1$) with one of the parental genotypes of the $F_1$ hybrid.

Crossing: The pollination of a female flower of a plant (i.e. strawberry plant), thereby resulting in the production of seed from the flower.

Cross-pollination: Fertilization by the union of two gametes from different plants.

$F_1$ Hybrid: The first generation progeny of the cross of two plants.

Genetic Complement: An aggregate of nucleotide sequences, the expression of which sequences defines the phenotype in strawberry plants, or components of plants including cells or tissue.

Genotype: The genetic constitution of a cell or organism.

Linkage: A phenomenon wherein alleles on the same chromosome tend to segregate together more often than expected by chance if their transmission was independent.

Marker: A readily detectable phenotype, preferably inherited in codominant fashion (both alleles at a locus in a diploid heterozygote are readily detectable), with no environmental variance component, i.e., heritability of 1.

Non-transgenic mutation: A mutation that is naturally occurring (spontaneous), or induced by conventional methods (e.g. exposure of plants to radiation or mutagenic compounds), not including mutations made using recombinant DNA techniques.

Octoploid: A cell or organism having eight sets of chromosomes

Phenotype: The detectable characteristics of a cell or organism in which the characteristics are the manifestation of gene expression.

Progeny: A descendant or descendants of a plant, developed as a result of the breeding of two individual plants or from selfing. The two individual plants used for breeding may be plants of the same genotype or may be plants of two distinct genotypes. During selfing, in some embodiments, the same plant may act as the donor of both male and female gametes. A descendant may be, for example, an F1 generation, an F2 generation, or any subsequent generation seed or plant, or part thereof Quantitative Trait Loci (QTL): Genetic loci that contribute, at least in part, certain numerically representable traits that are usually continuously distributed.

Regeneration: The development of a plant from tissue culture.

SSR profile: A profile of simple sequence repeats used as genetic markers and scored by gel electrophoresis following PCR amplification using flanking oligonucleotide primers.

Self-pollination: The transfer of pollen from the anther to the stigma of the same plant.

Single Locus Converted (Conversion) Plant: Plants that are developed by a plant breeding technique called backcrossing or by genetic engineering of a locus, wherein essentially all of the morphological and physiological characteristics of a plant are recovered in addition to the characteristics conferred by the single locus transferred into the plant via the backcrossing or genetic engineering technique.

Substantially Equivalent: A characteristic that, when compared, does not show a statistically significant difference (e.g., p=0.05) from the mean.

Tissue Culture: A composition comprising isolated cells of the same or a different type or a collection of such cells organized into parts of a plant.

Transgene: A genetic sequence that has been introduced into the nuclear or chloroplast genome of a strawberry plant by genetic transformation or site-specific modification.

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

Strawberry Variety 'FL 20.34-183'

The disclosure provides strawberry plants having the distinctive characteristics of the new strawberry variety 'FL 20.34-183' set forth herein and methods of using the same.

A. Origin and Breeding History

The new variety 'FL 20.34-183' originated in a strawberry breeding plot in Balm, Florida. The seed parent was 'FL 17.24-18' (unpatented), an unreleased breeding selection with excellent fruit size and yield. The pollen parent was 'FL 17.17-127' (unpatented) an unreleased breeding selection with excellent fruit flavor, shape and color. The seeds resulting from the controlled hybridization were germinated in a greenhouse, and the resulting seedlings were planted and allowed to produce daughter plants by asexual propagation (i.e. by runners). Two daughter plants from each seedling were transplanted to raised beds, where they fruited. 'FL 20.34-183' was selection number 183 of the 34th cross in the 2020-2021 seedling trial, and thus was given the breeding trial designation of 'FL 20.34-183'. The new variety 'FL 20.34-183' exhibited high early yields of consistently shaped and large fruit. 'FL 20.34-183' has been asexually propagated annually by runners; and test plantings have established that the vegetative and fruit characteristics of the propagules are identical to those of the initial daughter plants.

The new variety 'FL 20.34-183' can be distinguished from its seed parent 'FL 17.24-18' at least by its more intense fruit flavor and darker red color. 'FL 20.34-183' can also be distinguished from its pollen parent 'FL 17.17-127' at least by its greater fruit size and yield. When grown in a subtropical climate during the fall, winter, or a combination thereof, the new strawberry variety 'FL 20.34-183' can be distinguished from all other strawberry plants by at least the following characteristics: consistently well-shaped conical fruit; large fruit size; and high early yields.

Currently, 'Florida Brilliance' (U.S. Plant Pat. No. 30,564) and 'Florida127' (U.S. Plant Pat. No. 25,574), are the two dominant strawberries varieties in Hillsborough County, Florida. The new variety 'FL 20.34-183' has larger fruit size than 'Florida Brilliance' (FIG. 2), but with higher yields than 'Florida127' (FIG. 2). The new variety 'FL 20.34-183' is also more resistant to *Phytophthora* root and crown rots (caused by *Phytophthora cactorum*) than both commercial varieties 'Florida Brilliance' and 'Florida127'. However, 'FL 20.34-183' is more susceptible to crown rot (caused by *Colletotrichum gloeosporioides*) than these commercial varieties.

B. Phenotypic Description

In accordance with another aspect of the present invention, there is provided a strawberry plant having the physiological and morphological characteristics of strawberry variety 'FL 20.34-183'. A description of the exemplary morphological and physiological characteristics of strawberry variety 'FL 20.34-183' is presented below.

The characteristics described below have been repeatedly observed and can be used to distinguish strawberry variety 'FL 20.34-183' as a new and distinct variety of strawberry plant. Strawberry variety 'FL 20.34-183' has not been observed under all possible environmental conditions. Phenotype may vary due to environmental influence without variation in genotype. Strawberry variety 'FL 20.34-183' shows uniformity and stability within the limits of environmental influence for the traits described herein. No variant traits have been observed or are expected in 'FL 20.34-183'.

The following detailed botanical description sets forth the distinctive characteristics of the new strawberry variety 'FL 20.34-183'. The present botanical description is of 'FL 20.34-183' when grown under the ecological conditions that prevail during the winter production season in Balm, Florida, i.e., warm days and cool nights. Colors are objectively described using the CIELAB color scale (originally published by the International Commission on Illumination (CIE) in 1976) as measured using a Minolta Chroma Meter CR-400 (Minolta, Ramsey, NJ) colorimeter with a 1 cm aperture, calibrated against a white tile (Y=85.5, x=0.3164, y=0.3237). When the CIELAB color designations differ from the accompanying photographs, the CIELAB color designations are accurate.

Botanical classification: Strawberry (*Fragaria×ananassa* Duchesne)
Common name: Strawberry
Variety name—'FL 20.34-183'

Parentage
- Female parent.—'FL 17.24-18', not patented.
- Male parent.—'FL 17.17-127', not patented.

Plant Description
- Average height: 25 cm to 30 cm.
- Average width: 42 cm to 47 cm.
- Growth habit: Semi-upright.
- Number of crowns per plant: 6 to 9, depending on seasonal conditions.
- Vigor: Medium.

Leaves
- Overall description: Pinnately compound with three leaflets.

Petiole
- Average length: Approximately 19.6 cm.
- Average diameter: Approximately 3.3 mm.
- Pubescence: Light.
- Pubescence density: Sparse to Medium.
- Pose of hairs: Perpendicular.
- Texture: Smooth.
- Anthocyanin presence: Absent.
- Color: Light green (L*=57.31, a*=−18.79, b*=37.13).

Petiolule
- Length, terminal leaflet: Approximately 12.5 mm.
- Length, lateral leaflets: Approximately 7.0 mm.
- Diameter: Approximately 1.0 mm.
- Color: Light green (L*=47.84, a*=−12.19, b*=28.86).

Stipule
- Length: 41 mm to 45 mm.
- Width: 15-25 mm along the base of the petiole attachment.
- Anthocyanin presence: Absent.
- Color: Light green (L*=70.61, a*=−10.04, b*=27.65).

Terminal Leaflet
- Average length: Approximately 68 mm.
- Average breadth: Approximately 58 mm.
- Length/width ratio: Approximately 1.17.
- Shape in cross section: Slightly concave.
- Color, upper surface: Medium-light green (L*=37.55, a*=−14.68, b*=19.31).
- Color, lower surface: Light green (L*=51.41, a*=−13.15, b*=22.23).
- Glossiness: Slight gloss.
- Base shape: Cuneate.
- Apex descriptor: Rounded.
- Pubescence density: Sparse to moderate.
- Texture: Moderately smooth.
- Venation pattern: Pinnate.

Secondary Leaflets
- Average length: Approximately 67 mm.
- Average breadth: Approximately 64 mm.
- Length/width ratio: Approximately 1.05.
- Shape in cross section: Slightly concave.
- Color, upper surface: Medium-light green (L*=37.84, a*=−14.95, b*=19.85).
- Color, lower surface: Light green (L*=51.18, a*=−14.10, b*=21.70).
- Glossiness: Slight gloss.
- Base shape: Oblique rounded.
- Apex descriptor: Obtuse.
- Pubescence density: Sparse to moderate.
- Texture: Moderately smooth.
- Venation pattern: Pinnate.

Leaflet Margins

Crenate, with an average of 23 and 28 serrations per terminal and secondary leaflet, respectively.

Stolons

Number of daughter plants: 15 to 40, depending on environmental conditions.

Anthocyanin presence: Occasional.

Thickness: 2 mm to 3 mm.

Pubescence: Light with pose of hairs ascending.

Inflorescences

Time of flowering: Partial remontancy, commencing two weeks after establishment and continually thereafter in suitable climate.

Flower number per plant: 45 to 60 flowers over a 4-month Florida growing season.

Flower height: 0 to 18 cm above soil surface depending on angle of pedicel.

Position relative to canopy: Flowers open slightly below canopy height.

Branching of the inflorescence: At or very close to the crown.

Petals

Number: Approximately 5.

Length: Approximately 11 mm.

Width: 10 to 11 mm.

Shape: Orbicular.

Apex: Rounded.

Base: Rounded.

Margin: Smooth.

Average diameter of the corolla (i.e. the petals collectively): 34 mm.

Average number of stamens: 25.

Color, upper surface: White (L*=80.87, a*=–2.12, b*=4.48).

Color, lower surface: White (L*=81.86, a*=–3.59, b*=8.58).

Calyx

Diameter: 35-40 mm.

Diameter of calyx relative to corolla: 0%-10% greater in diameter.

Diameter of calyx relative to the fruit: 0%-10% greater in diameter.

Insertion of calyx: Level to slightly inserted.

Color: Medium-light green (L*=53.77, a*=–12.94, b*=31.66).

Sepals

Number per flower: 10-11.

Length: 13-16 mm.

Width: 6-7 mm.

Apex: Subacute to lobed.

Margin: Smooth.

Color, upper surface: Medium green (L*=40.71, a*=–18.69, b*=26.34).

Color, lower surface: Light green (L*=52.39, a*=–15.41, b*=24.46).

Pedicels

Attached to mature primary fruit and 14 cm to 24 cm in length and 2 to 3 mm in diameter depending on the time of the season. At peak production, the plant will have several crowns, each producing a truss. Each truss will have 5 to 8 pedicels. Inflorescences branch very close to the crown, rendering the peduncle rarely visible.

Fruit

Number per truss: 5 to 7.

Shape: Medium conical to cordate.

Average fruit weight: 25 to 28 g (as shown in FIG. 2).

Weight, primary fruit: 30 to 50 g.

Weight, secondary and tertiary fruit: 16 to 35 g.

Length, primary fruit: 47 to 57 mm.

Width, primary fruit: 42 to 47 mm.

Fruit flavor: Slightly higher sweetness and flavor compared to 'Florida Brilliance'.

Fruit firmness: Similar to commercial standard 'Florida Brilliance'.

Fruit cavity: Rare.

Achenes: Slightly sunken, 120 to 300 per fruit.

External fruit color: Glossy medium red (a*=35.94).

Internal fruit color: Medium red (a*=24.78).

Evenness of color: Very consistently even.

Flesh and skin firmness at full ripe stage: Very firm.

Rain damage: Similar to 'Florida Brilliance'.

Early Yield

Similar to 'Florida Brilliance' (as shown in FIG. 2).

Preferred Planting Period

October $10^{th}$ to October $20^{th}$ in West Central Florida.

Nursery Performance

Produces similar runners to commercial standards of known varieties.

Disease resistance:

*Phytophthora* crown rot (caused by *Phytophthora cactorum*): Moderately resistant.

Powdery mildew (caused by *Podosphaera aphanis*): Moderately resistant.

Anthracnose fruit rot (caused by *Colletotrichum acutatum*): Moderately resistant.

Charcoal rot (caused by *Macrophomina phaseolina*): Moderately susceptible.

C. Deposit Information

A deposit of representative sample of plant tissue of strawberry variety 'FL 20.34-183' was made with the Provasoli-Guillard National Center for Marine Algae and Microbiota (NCMA), 60 Bigelow Drive, East Boothbay, Maine, 04544 USA. The deposit was assigned NCMA Accession No. 202402001. The date of deposit of the representative sample of plant tissue with the NCMA was Feb. 6, 2024. The deposit has been accepted under the Budapest Treaty and will be maintained in the NCMA depository for a period of 30 years, or 5 years after the most recent request, or for the enforceable life of the patent, whichever is longer, and will be replaced if necessary during that period. Upon issuance, all restrictions on the availability to the public of the deposit will be irrevocably removed consistent with all of the requirements of the Budapest Treaty and 37 C.F.R. §§ 1.801-1.809. Applicant does not waive any infringement of rights granted under this patent or under the Plant Variety Protection Act (7 USC 2321 et seq.).

Further Embodiments of the Invention

A. Processes of Crossing Strawberry Plants and the Strawberry Plants Produced by Such Crosses The present invention provides processes of preparing novel strawberry plants and strawberry plants produced by such processes. In accordance with such a process, a first parent strawberry plant may be crossed with a second parent strawberry plant wherein at least one of the first and second strawberry plants is a plant of strawberry variety 'FL 20.34-183'. One application of the process is in the production of $F_1$ hybrid plants. Another important aspect of this process is that it can be used for the development of novel strawberry varieties (also known as cultivars and lines). For example, the strawberry variety 'FL 20.34-183' could be crossed to any compatible second plant, and the resulting hybrid progeny could be vegetatively propagated or the hybrid progeny could be each selfed or further crossed for about 5 to 7 or more generations, thereby providing a large number of distinct varieties. These varieties could then be crossed with other varieties and the resulting hybrid progeny analyzed for beneficial characteristics. In this way, novel varieties conferring desirable characteristics could be identified. "Vegetative propagation" as used herein refers to any form of asexual reproduction occurring in plants in which a new plant grows from a fragment of the parent plant. Non-limiting examples of vegetative propagation methods include tissue culture and division.

Strawberry (*Fragaria×ananassa* Duchesne) is a heterozygous allo-octoploid (2n=8×=56) species. Hundreds of strawberry varieties are known to those of skill in the art, many one of which could be crossed with strawberry variety 'FL 20.34-183' to produce a hybrid plant. For example, the U.S. Department of Agriculture, Agricultural Research Service (USDA-ARS), National Clonal Germplasm Repository at Corvallis, Oregon houses the *Fragaria* genebank for the U.S. National Plant Germplasm System (NPGS). This collection includes 411 unique *F.×ananassa* Duch. cultivars and selections in addition to 1079 representatives of 33 taxa from 29 countries. The clonal germplasm is maintained as potted plants growing in screenhouses and backed up as in vitro cultures stored for up to 5 years at 4° C. Seeds for wild species are preserved at −20° C.

When the strawberry variety 'FL 20.34-183' is crossed with another strawberry plant to yield a hybrid, it can serve as either the maternal or paternal plant. Depending on the seed production characteristics relative to a second parent in a hybrid cross, it may be desired to use one of the parental plants as the male or female parent. Therefore, a decision to use one parent plant as a male or female may be made based on any such characteristics as is well known to those of skill in the art.

B. Breeding Strawberry Plants

Another aspect of the current invention concerns methods for crossing the strawberry variety 'FL 20.34-183' with itself or a second plant and the seeds and plants produced by such methods. These methods can be used for propagation of variety 'FL 20.34-183', or can be used to produce hybrid strawberry seeds and the plants grown therefrom. Hybrid seeds are produced by crossing variety 'FL 20.34-183' with second strawberry parent line. Plants derived from strawberry variety 'FL 20.34-183' may be used, in certain embodiments, for the development of new strawberry varieties.

The development of new varieties using one or more starting varieties is well known in the art. In accordance with the invention, novel varieties may be created by crossing variety 'FL 20.34-183' followed by multiple generations of breeding according to such well known methods. New varieties may be created by crossing with any second plant. In selecting such a second plant to cross for the purpose of developing a novel variety, it may be desired to choose those plants which either themselves exhibit one or more selected desirable characteristics or which exhibit the desired characteristic(s) in progeny. Once initial crosses have been made, inbreeding and/or selection take place to produce new varieties.

Uniform lines of new varieties may also be developed by way of double-haploids. This technique allows the creation of true breeding lines without the need for multiple generations of selfing and selection. In this manner, true breeding lines can be produced in as little as one generation. Haploid embryos may be produced from microspores, pollen, anther cultures, or ovary cultures. The haploid embryos may then be doubled autonomously, or by chemical treatments (e.g. colchicine treatment). Alternatively, haploid embryos may be grown into haploid plants and treated to induce chromosome doubling. In either case, fertile homozygous plants are obtained. In accordance with the invention, any of such techniques may be used in connection with variety 'FL 20.34-183' and progeny thereof to achieve a homozygous line. See, e.g Niemirowicz-Szczytt, K. Strawberry (*Fragaria×ananassa* Duch.): In Vitro Production of Haploids. In: Bajaj, Y. P. S. (eds) Haploids in Crop Improvement I. Biotechnology in Agriculture and Forestry, vol 12. (1990); and Hennerty, M. J., et al. Polyhaploidy in strawberry. In: Jain, S. M., Sopory, S. K., Veilleux, R. E. (eds) In Vitro Haploid Production in Higher Plants. *Current Plant Science and Biotechnology in Agriculture*, vol 25. (1996).

New varieties may be created, for example, by crossing variety 'FL 20.34-183' with any second plant and selection of progeny in various generations and/or by doubled haploid technology. In choosing a second plant to cross for the purpose of developing a novel variety, it may be desired to choose those plants which either themselves exhibit one or more selected desirable characteristics or which exhibit the desired characteristic(s) in progeny.

In certain aspects of the invention, plants described herein are provided modified to include at least a first desired heritable trait. Such plants may, in one embodiment, be developed by a plant breeding technique called backcrossing, wherein essentially all of the physiological and morphological characteristics of a variety are recovered in addition to a genetic locus transferred into the plant via the backcrossing technique. The term single locus converted plant as used herein refers to those strawberry plants which are developed by a plant breeding technique called backcrossing or by genetic engineering, wherein essentially all of the desired physiological and morphological characteristics of a variety are recovered or conserved in addition to the single locus introduced into the variety via the backcrossing or genetic engineering technique, respectively. By essentially all of the morphological and physiological characteristics, it is meant that the characteristics of a plant are recovered or conserved that are otherwise present when compared in the same environment, other than an occasional variant trait that might arise during backcrossing, introduction of a transgene, or application of a genetic engineering technique.

Backcrossing methods can be used with the present invention to improve or introduce a characteristic into the present variety. The parental strawberry plant which contributes the locus for the desired characteristic is termed the nonrecurrent or donor parent. This terminology refers to the fact that the nonrecurrent parent is used one time in the backcross protocol and therefore does not recur. The parental strawberry plant to which the locus or loci from the nonrecurrent parent are transferred is known as the recurrent parent as it is used for several rounds in the backcrossing protocol.

In a typical backcross protocol, the original variety of interest (recurrent parent) is crossed to a second variety (nonrecurrent parent) that carries the single locus of interest to be transferred. The resulting progeny from this cross are then crossed again to the recurrent parent and the process is repeated until a strawberry plant is obtained wherein essentially all of the desired physiological and morphological characteristics of the recurrent parent are recovered in the converted plant, in addition to the single transferred locus from the nonrecurrent parent.

The selection of a suitable recurrent parent is an important step for a successful backcrossing procedure. The goal of a backcross protocol is to alter or substitute a single trait or characteristic in the original variety. To accomplish this, a single locus of the recurrent variety is modified or substituted with the desired locus from the nonrecurrent parent, while retaining essentially all of the rest of the desired genetic, and therefore the desired physiological and morphological constitution of the original variety. The choice of the particular nonrecurrent parent will depend on the purpose of the backcross; one of the major purposes is to add some commercially desirable trait to the plant. The exact backcrossing protocol will depend on the characteristic or trait being altered and the genetic distance between the recurrent and nonrecurrent parents. Although backcrossing methods are simplified when the characteristic being transferred is a dominant allele, a recessive allele, or an additive allele (between recessive and dominant), may also be transferred. In this instance it may be necessary to introduce a test of the progeny to determine if the desired characteristic has been successfully transferred.

In one embodiment, progeny strawberry plants of a backcross in which a plant described herein is the recurrent parent comprise (i) the desired trait from the non-recurrent parent and (ii) all of the physiological and morphological characteristics of strawberry recurrent parent as determined at the 5% significance level when grown in the same environmental conditions.

New varieties can also be developed from more than two parents. The technique, known as modified backcrossing, uses different recurrent parents during the backcrossing. Modified backcrossing may be used to replace the original recurrent parent with a variety having certain more desirable characteristics or multiple parents may be used to obtain different desirable characteristics from each.

With the development of molecular markers associated with particular traits, it is possible to add additional traits into an established germ line, such as represented here, with the end result being substantially the same base germplasm with the addition of a new trait or traits. Molecular breeding, as described in Moose and Mumm, 2008 (*Plant Physiology,* 147: 969-977), for example, and elsewhere, provides a mechanism for integrating single or multiple traits or QTL into an elite line. This molecular breeding-facilitated movement of a trait or traits into an elite line may encompass incorporation of a particular genomic fragment associated with a particular trait of interest into the elite line by the mechanism of identification of the integrated genomic fragment with the use of flanking or associated marker assays. In the embodiment represented here, one, two, three or four genomic loci, for example, may be integrated into an elite line via this methodology. When this elite line containing the additional loci is further crossed with another parental elite line to produce hybrid offspring, it is possible to then incorporate at least eight separate additional loci into the hybrid. These additional loci may confer, for example, such traits as a disease resistance or a bulb quality trait. In one embodiment, each locus may confer a separate trait. In another embodiment, loci may need to be homozygous and exist in each parent line to confer a trait in the hybrid. In yet another embodiment, multiple loci may be combined to confer a single robust phenotype of a desired trait.

Many single locus traits have been identified that are not regularly selected for in the development of a new inbred but that can be improved by backcrossing techniques. Single locus traits may or may not be transgenic; examples of these traits include, but are not limited to, male sterility, herbicide resistance, resistance to bacterial, fungal, or viral disease, insect resistance, restoration of male fertility, modified fatty acid or carbohydrate metabolism, and altered nutritional quality. These comprise genes generally inherited through the nucleus.

Direct selection may be applied where the single locus acts as a dominant trait. For this selection process, the progeny of the initial cross are assayed for viral resistance or the presence of the corresponding gene prior to the backcrossing. Selection eliminates any plants that do not have the desired gene and resistance trait, and only those plants that have the trait are used in the subsequent backcross. This process is then repeated for all additional backcross generations.

Selection of strawberry plants for breeding is not necessarily dependent on the phenotype of a plant and instead can be based on genetic investigations. For example, one can utilize a suitable genetic marker which is closely genetically linked to a trait of interest. One of these markers can be used to identify the presence or absence of a trait in the offspring of a particular cross, and can be used in selection of progeny for continued breeding. This technique is commonly referred to as marker assisted selection. Any other type of genetic marker or other assay which is able to identify the relative presence or absence of a trait of interest in a plant can also be useful for breeding purposes. Procedures for marker assisted selection applicable to the breeding of strawberry are well known in the art. Such methods will be of particular utility in the case of recessive traits and variable phenotypes, or where conventional assays may be more expensive, time consuming or otherwise disadvantageous. In addition, marker assisted selection may be used to identify plants comprising desirable genotypes at the seed, seedling, or plant stage, to identify or assess the purity of a variety, to catalog the genetic diversity of a germplasm collection, and to monitor specific alleles or haplotypes within an established variety.

Types of genetic markers which could be used in accordance with the invention include, but are not necessarily limited to, Simple Sequence Length Polymorphisms (SSLPs) (Williams et al., *Nucleic Acids Res.,* 1 8: 6531-6535, 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., *Science,* 280: 1077-1082, 1998).

In particular embodiments of the invention, marker assisted selection is used to increase the efficiency of a backcrossing breeding scheme for producing a strawberry plant comprising a desired trait. This technique is commonly referred to as marker assisted backcrossing (MABC). This technique is well-known in the art and may involve, for example, the use of three or more levels of selection, including foreground selection to identity the presence of a desired locus, which may complement or replace phenotype screening protocols; recombinant selection to minimize linkage drag; and background selection to maximize recurrent parent genome recovery.

The variety of the present invention is particularly well suited for the development of new varieties based on the elite nature of the genetic background of variety 'FL 20.34-183'. In selecting a second plant to cross with variety 'FL 20.34-183' for the purpose of developing novel strawberry varieties, it will typically be preferred to choose those plants which either themselves exhibit one or more selected desirable characteristics or which exhibit the desired characteristic(s) when in hybrid combination. Examples of desirable characteristics may include, but are not necessarily limited to, improved fruit size, firmness, yield, enhanced flavor, for example increased sweetness; optimized acidity (i.e. titratable acidity); optimized metabolite profiles, for example sugars, furanones, esters, lactones, terpenoids, aldehydes, sulfur compounds; increased resistance to viral pathogens; increased resistance to one or more bacterial pathogens; increased resistance to one or more fungal diseases; increased resistance to insects; optimized soluble solids content (SSC); and the like. See, e. g. Porter, M., Fan, Z., Lee, S., & Whitaker, V. M. Strawberry breeding for improved flavor. *Crop Science,* 63, 1949-1963 (2023).

Furthermore, examples of desirable characteristics may also include, in specific embodiments, high strawberry yield, disease tolerance or resistance, and adaptability for soil and climate conditions. Consumer-driven traits, such as fruit shape, color, texture, and taste are other examples of traits that may be incorporated into new varieties of strawberry plants developed by this invention.

C. Genetically Identifying Strawberry Varieties

In an embodiment, the present invention provides a strawberry variety characterized by the molecular and physiological data obtained from a representative sample of said variety deposited with the Provasoli-Guillard National Center for Marine Algae and Microbiota (NCMA). Thus, plants, seeds, or parts thereof, having all of the morphological and physiological characteristics of strawberry variety 'FL 20.34-183' are provided.

In some examples, a plant, a plant part, or a seed of strawberry variety 'FL 20.34-183' may be characterized by producing a molecular profile. A molecular profile may include, but is not limited to, one or more genotypic and/or phenotypic profile(s). A genotypic profile may include, but is not limited to, a marker profile, such as a genetic map, a linkage map, a trait maker profile, a SNP profile, an SSR profile, a genome-wide marker profile, a haplotype, or the like. A molecular profile may also be a nucleic acid sequence profile, and/or a physical map. A phenotypic profile may include, but is not limited to, a protein expression profile, a metabolic profile, an mRNA expression profile, and the like.

One means of generating genetic marker profiles is to assay SNPs that are known in the art. Thousands of SNPs are known in strawberry, see, e.g., Bassil, N. V. et al. Development and preliminary evaluation of a 90 K Axiom SNP array for the allo-octoploid cultivated strawberry *Fragaria×ananassa*. BMC Genomics, 16 (1), 1310; (2015). A marker system based on SNPs can be highly informative in linkage analysis relative to other marker systems, in that multiple alleles may be present. Another advantage is that SNPs can be detected through use of strategically designed primers, probes, or other specially designed hybridization molecules, which eliminates the need to perform labor-intensive Southern blots. Further, many SNP detection methods are easily scalable and therefore can easily integrate into high-throughput analysis platforms such as microarray and next-generation sequencing technologies. High density microarray platforms, for example, are capable of analyzing hundreds of thousands SNPs on a single microarray chip.

A genotypic profile of strawberry variety 'FL 20.34-183' can be used to identify a plant or population of plants comprising variety 'FL 20.34-183' as a parent, because such plants will comprise the same allelic profile as variety 'FL 20.34-183' at an expected frequency by Mendelian inheritance. In addition, plants and plant parts substantially benefiting from the use of variety 'FL 20.34-183' in their development, such as variety 'FL 20.34-183' comprising a backcross conversion, transgene, and the like, may be identified by having a molecular marker profile with a high percent identity to variety 'FL 20.34-183'.

A genotypic profile of strawberry variety 'FL 20.34-183' also can be used to identify essentially derived varieties and other progeny varieties developed from the use of strawberry variety 'FL 20.34-183', as well as cells and other plant parts thereof. Plants of the invention include any plant having at least 90%, 91%, 92%, 93%, 94%, 95%, 96%, 97%, 98%, 99%, 99.5%, or 99.9% of the markers in the genotypic profile, and that retain 90%, 91%, 92%, 93%, 94%, 95%, 96%, 97%, 98%, 99%, 99.5%, or 99.9% of the morphological and physiological characteristics of strawberry variety 'FL 20.34-183' when grown under the same conditions. Such plants may be developed using markers well known in the art. Progeny plants and plant parts produced using strawberry variety 'FL 20.34-183' may be identified by any means known in the art that is indicative or consistent with the variety. For example, progeny plants and plant parts produced using strawberry variety 'FL 20.34-183' may be identified by having a molecular marker profile of at least 25%, 30%, 35%, 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% genetic contribution from strawberry variety 'FL 20.34-183' by percent identity or percent similarity, or such plants may be identified by statistical genetic parameters. Unique molecular profiles may be identified with other next-generation sequencing tools, such as SNP discovery or haplotype analysis.

D. Plants Derived by Genetic Engineering

Various genetic engineering technologies have been developed and may be used by those of skill in the art to introduce traits in plants. In certain aspects of the claimed invention, traits are introduced into strawberry plants via altering or introducing a single genetic locus or transgene into the genome of a recited variety or progenitor thereof. Methods of genetic engineering to modify, delete, or insert genes and polynucleotides into the genomic DNA of plants are well-known in the art.

In specific embodiments of the invention, improved strawberry plants can be created through the site-specific modification of a plant genome. Methods of genetic engineering include, for example, utilizing sequence-specific nucleases such as zinc-finger nucleases (see, for example, U.S. Pat. Appl. Pub. No. 2011-0203012); engineered or native meganucleases; TALE-endonucleases (see, for example, U.S. Pat. Nos. 8,586,363 and 9,181,535); and RNA-guided endonucleases, such as those of the CRISPR/Cas systems (see, for example, U.S. Pat. Nos. 8,697,359 and 8,771,945 and U.S. Pat. Appl. Pub. No. 2014-0068797). One embodiment of the invention thus relates to utilizing a nuclease or any associated protein to carry out genome modification. This nuclease could be provided heterologously within donor template DNA for templated-genomic editing or in a separate molecule or vector. A recombinant DNA construct may also comprise a sequence encoding one or more guide RNAs to direct the nuclease to the site within the plant genome to be modified. Further methods for altering or introducing a single genetic locus include, for example, utilizing single-stranded oligonucleotides to introduce base pair modifications in an strawberry plant genome (see, for example Sauer et al., *Plant Physiol,* 170 (4): 1917-1928, 2016 and Wang et al., *Int J Mol Sci.* 20 (19): 4702, 2019).

Methods for site-directed alteration or introduction of a single genetic locus are well-known in the art and include those that utilize sequence-specific nucleases, such as the aforementioned, or complexes of proteins and guide-RNA that cut genomic DNA to produce a double-strand break (DSB) or nick at a genetic locus. As is well-understood in the art, during the process of repairing the DSB or nick introduced by the nuclease enzyme, a donor template, transgene, or expression cassette polynucleotide may become integrated into the genome at the site of the DSB or nick. The presence of homology arms in the DNA to be integrated may promote the adoption and targeting of the insertion sequence into the plant genome during the repair process through homologous recombination or non-homologous end joining (NHEJ).

In another embodiment of the invention, genetic transformation may be used to insert a selected transgene into a plant of the disclosure or may, alternatively, be used for the preparation of transgenes which can be introduced by backcrossing. Methods for the transformation of plants that are well known to those of skill in the art and applicable to many plant species include, but are not limited to, electroporation, microprojectile bombardment, *Agrobacterium*-mediated transformation and direct DNA uptake by protoplasts. For example, Zakaria H et al. Improved regeneration and transformation protocols for three strawberry cultivars. GM Crops Food. 2014 January-March; 5(1): 27-35.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

Many useful traits are those which are introduced by genetic transformation techniques. Methods for the genetic transformation of strawberry are known to those of skill in the art. For example, methods which have been described for the genetic transformation of strawberry may include electroporation, electrotransformation, microprojectile bombardment, *Agrobacterium*-mediated transformation, direct DNA uptake transformation of protoplasts and silicon carbide fiber-mediated transformation. See, e.g., Khachatourians et al., (In: *Transgenic Plants and Crops*, Marcel Dekker, Inc., 2002).

It is understood to those of skill in the art that a transgene need not be directly transformed into a plant, as techniques for the production of stably transformed strawberry plants that pass single loci to progeny by Mendelian inheritance is well known in the art. Such loci may therefore be passed from parent plant to progeny plants by standard plant breeding techniques that are well known in the art. Examples of traits that may be introduced into a strawberry plant according to the invention include, for example, male sterility, herbicide resistance, disease resistance, insect resistance, and enhanced nutritional quality.

An efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large. Microprojectile bombardment techniques are widely applicable, and may be used to transform virtually any plant species. See, e.g. Macarena Cordero de Mesa et al. *Australian Journal of Plant Physiology* 27(12) 1093-1100 (2000).

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations. Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (U.S. Pat. No. 5,563,055, incorporated herein by reference in its entirety). Transformation of plant protoplasts also can be achieved using methods based on calcium phosphate precipitation, polyethylene glycol treatment, electroporation, and combinations of these treatments.

A number of promoters have utility for plant gene expression for any gene of interest including but not limited to selectable markers, scoreable markers, genes for pest and disease resistance, and any other gene of agronomic interest. Examples of constitutive promoters useful for driving gene expression in plants include, but are not limited to, the cauliflower mosaic virus (CaMV) P-35S promoter, which confers constitutive, high-level expression in most plant tissues, including monocots; a tandemly duplicated version of the CaMV 35S promoter, the enhanced 35S promoter (P-e35S) the nopaline synthase promoter, the octopine synthase promoter; and the figwort mosaic virus (P-FMV) promoter as described in U.S. Pat. No. 5,378,619 (incorporated herein by reference in its entirety), and an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, and other plant DNA virus promoters known to express in plant cells.

A variety of plant gene promoters that are regulated in response to environmental, hormonal, chemical, and/or developmental signals can be used for expression of an operably linked gene in plant cells, including promoters regulated by (1) heat, (2) light (e.g., pearbcS-3A promoter; maize rbcS promoter; or chlorophyll a/b-binding protein promoter), (3) hormones, such as abscisic acid, (4) wounding (e.g., wunl); or (5) chemicals such as methyl jasmonate, salicylic acid, or Safener. It may also be advantageous to employ organ-specific promoters.

Exemplary nucleic acids which may be introduced to the plants of this disclosure include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a strawberry plant according to the invention. Non-limiting examples of particular genes and corresponding phenotypes one may choose to introduce into a plant of the disclosure include one or more genes for insect tolerance, such as a *Bacillus thuringiensis* (B.t.) gene, pest tolerance such as genes for fungal disease control, herbicide tolerance such as genes conferring glyphosate tolerance, and genes for quality improvements such as environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, U.S. Pat. Nos. 5,689,052, 5,500,365 and 5,880,275, each of which are herein incorporated by reference in their entirety. In another embodiment, the structural gene can confer tolerance to the herbicide glyphosate as conferred by genes including, but not limited to *Agrobacterium* strain C'P4' glyphosate resistant EPSPS gene (aroA: C'P4') as described in U.S. Pat. No. 5,633,435, herein incorporated by reference in its entirety, or glyphosate oxidoreductase gene (GOX) as described in U.S. Pat. No. 5,463,175, herein incorporated by reference in its entirety.

Alternatively, the DNA coding sequences can affect these phenotypes by encoding a non-translatable RNA molecule that causes the targeted inhibition of expression of an endogenous gene, for example via antisense-or co-suppression-mediated mechanisms. The RNA could also be a catalytic RNA molecule (i.e., a ribozyme) engineered to cleave a desired endogenous mRNA product. Thus, any gene which produces a protein or mRNA which expresses a phenotype or morphology change of interest is useful for the practice of the present disclosure.

E. Additional Traits

Additional traits can be introduced into the strawberry variety of the present invention. A non-limiting example of such a trait is a coding sequence that decreases RNA and/or protein levels. The decreased RNA and/or protein levels may be achieved through RNAi methods, such as those described in U.S. Pat. No. 6,506,559 to Fire and Mellow.

Another trait that may find use with the strawberry variety of the invention is a sequence that allows for site-specific recombination. Examples of such sequences include the FRT sequence, used with the FLP recombinase (Zhu and Sadowski, *J. Biol. Chem.*, 270: 23044-23054, 1995); and the LOX sequence, used with CRE recombinase (Sauer, *Mol. Cell. Biol.*, 7: 2087-2096, 1987). The recombinase genes can be encoded at any location within the genome of the strawberry plant, and are active in the hemizygous state.

It may also be desirable to make strawberry plants more tolerant to or more easily transformed with *Agrobacterium tumefaciens*. Expression of p53 and iap, two baculovirus cell-death suppressor genes, inhibited tissue necrosis and DNA cleavage. Additional targets can include plant-encoded proteins that interact with the *Agrobacterium* Vir genes; enzymes involved in plant cell wall formation; and histones, histone acetyltransferases and histone deacetylases (reviewed in Gelvin, *Microbiology* & *Mol. Biol. Reviews,* 67: 16-37, 2003).

F. Plants Comprising Non-Transgenic Mutations

In still yet another aspect, a plant of strawberry variety 'FL 20.34-183', further comprising a non-transgenic mutation is provided. The phrase "non-transgenic mutation" is used herein to refer to a mutation that is naturally occurring (spontaneous), or induced by conventional methods (e.g. exposure of plants to radiation or mutagenic compounds), not including mutations made using recombinant DNA techniques. Various mutagenesis techniques have been developed and may be used by those of skill in the art to induce mutations in plants. Methods of mutagenesis may include, for example, exposure to irradiation, mutagenic compounds, extreme heat, or tissue culture conditions; long-term seed storage; and targeting induced local lesions in genomes (TILLING). In some embodiments, ionizing radiation may be produced by X-rays, gamma rays, neutrons, beta rays, or ultraviolet rays. Non-limiting examples of chemical mutagens include base analogues, antibiotics, alkylating agents, sodium azide, hydroxylamine, nitrous acid, methyl-nitrilsourea, and acridines. Methods of mutagenesis to modify, delete, or insert polynucleotides into the genomic DNA are well-known in the art.

In one aspect, improved strawberry varieties may be created through mutation of the plant genome. In one embodiment, a plant of the strawberry variety 'FL 20.34-183' may be subjected to a mutagenesis technique to create a population of mutant plants. Such mutant plants, for example, may comprise a mutation and otherwise comprise all of the physiological and morphological characteristics of strawberry variety 'FL 20.34-183'.

G. Tissue Cultures and In Vitro Regeneration of Strawberry Plants

In another aspect, the invention relates to tissue cultures of the strawberry variety of the present disclosure. As used herein, the term "tissue culture" indicates a composition comprising isolated cells of the same or a different type or a collection of such cells organized into parts of a plant. Exemplary types of tissue cultures are protoplasts, calli and plant cells that are intact in plants or parts of plants, such as embryos, meristems, cotyledons, pollen, leaves, anthers, roots, root tips, pistil, flower, seed, stems, and the like. In a preferred embodiment, the tissue culture comprises cells derived from immature tissues of these plant parts. Means for preparing and maintaining plant tissue cultures are well known in the art (See, e.g. Naing, A. H. et al. In vitro propagation method for production of morphologically and genetically stable plants of different strawberry cultivars. *Plant Methods* 15, 36 (2019), incorporated herein by reference in their entirety).

In yet another aspect, compositions are provided comprising a cell of strawberry variety 'FL 20.34-183' comprised in plant cell growth media. Plant cell growth media are well known to those of skill in the art. Plant cell growth media can provide adequate support for plant cells, including providing moisture and/or nutritional components.

All of the compositions and methods disclosed and claimed herein can be made and executed without undue experimentation in light of the present disclosure. While the compositions and methods of this invention have been described in terms of the foregoing illustrative embodiments, it will be apparent to those of skill in the art that variations, changes, modifications, and alterations may be applied to the composition, methods, and in the steps or in the sequence of steps of the methods described herein, without departing from the true concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

The references cited herein, to the extent that they provide exemplary procedural or other details supplementary to those set forth herein, are specifically incorporated herein by reference.

What is claimed is:

1. A strawberry plant of variety 'FL 20.34-183', a representative sample of plant tissue of said variety having been deposited under NCMA Accession No. 202402001.

2. A plant part of the plant of claim 1, wherein said plant part comprises at least one strawberry variety 'FL 20.34-183' cell.

3. The plant part of claim 2, defined as a flower, a leaf, a cutting, a stem, or a fruit.

4. A strawberry plant, having all of the physiological and morphological characteristics of the plant of claim 1.

5. A tissue culture of regenerable cells of the plant of claim 1, wherein the tissue culture of regenerable cells comprises cells or protoplasts from a plant part selected from the group consisting of meristems, leaves, roots, root tips, and flowers.

6. A strawberry plant regenerated from the tissue culture of claim 5, wherein the regenerated plant comprises all of the physiological and morphological characteristics of strawberry variety 'FL 20.34-183', a sample of plant tissue of said variety having been deposited under NCMA Accession No. 202402001.

7. A method for producing a seed of a strawberry plant derived from strawberry variety 'FL 20.34-183', the method comprising the steps of:

(a) crossing the plant of claim 1 with itself or a second strawberry plant; and (b) allowing seed of a strawberry variety 'FL 20.34-183'-derived strawberry plant to form.

8. The method of claim 7, the method further comprising the steps of:

(c) crossing a plant grown from said 'FL 20.34-183'-derived strawberry seed with itself or a second strawberry plant to yield additional 'FL 20.34-183'-derived strawberry seed;

(d) growing said additional 'FL 20.34-183'-derived strawberry seed of step (c) to yield additional 'FL 20.34-183'-derived strawberry plants; and (e) repeating the crossing and growing steps of (c) and (d) to generate further 'FL 20.34-183'-derived strawberry plants.

9. A method of vegetatively propagating the plant of claim 1, the method comprising the steps of:

(a) collecting tissue capable of being propagated from the plant of claim 1; and (b) propagating a strawberry plant from the tissue.

10. A method of introducing a trait into a strawberry plant, the method comprising:

(a) utilizing the plant of claim 1 as a recurrent parent and crossing the plant of claim 1 with a donor strawberry plant that comprises the trait to produce F1 progeny;

(b) selecting an F1 progeny that comprises the trait;

(c) backcrossing the selected F1 progeny with the recurrent parent in step (a) to produce backcross progeny;

(d) selecting a backcross progeny that comprises the trait; and (e) repeating steps (c) and (d) at least one more time to produce a selected second or higher backcross progeny.

11. The method of claim 10, wherein the backcross progeny of step (e) comprises the trait and otherwise comprises all of the physiological and morphological characteristics of strawberry variety 'FL 20.34-183', a representative sample of plant tissue of said variety having been deposited under NCMA Accession No. 202402001.

12. A method of producing a strawberry plant comprising an added trait, the method comprising introducing by genetic transformation a transgene conferring the trait into the plant of claim 1.

13. A strawberry plant produced by the method of claim 12, wherein the strawberry plant comprises the transgene and otherwise comprises all of the physiological and morphological characteristics of strawberry variety 'FL 20.34-183'.

14. A strawberry plant of strawberry variety 'FL 20.34-183', a sample of plant tissue of said variety 'FL 20.34-183' having been deposited under NCMA Accession No. 202402001, further comprising a transgene and otherwise comprising all of the physiological and morphological characteristics of strawberry variety 'FL 20.34-183', wherein the transgene is introduced by genetic transformation or genetic engineering.

15. The plant of claim 14, wherein the transgene confers a trait selected from the group consisting of increased fruit size, improved fruit shape, increased firmness, increased yield, enhanced fruit flavor, and increased shelf-life, as compared to a strawberry plant of variety 'FL 20.34-183'.

16. A strawberry plant of strawberry variety 'FL 20.34-183', a sample of plant tissue of said variety 'FL 20.34-183' having been deposited under NCMA Accession No. 202402001, further comprising a single locus conversion and otherwise comprising all of the physiological and morphological characteristics of strawberry variety 'FL 20.34-183', wherein the single locus conversion is introduced by genetic transformation or genetic engineering.

17. The plant of claim 16, wherein the single locus conversion confers a trait selected from the group consisting of increased fruit size, improved fruit shape, increased firmness, increased yield, enhanced fruit flavor, and increased shelf-life, as compared to a strawberry plant of variety 'FL 20.34-183'.

18. A method of producing a strawberry fruit comprising:

(a) obtaining the plant of claim 1, wherein the plant has been cultivated to maturity, and (b) collecting at least one strawberry fruit from the plant.

* * * * *